United States Patent
Simonton et al.

(10) Patent No.: US 8,062,692 B2
(45) Date of Patent: Nov. 22, 2011

(54) METHODS FOR USING DENTAL COMPOSITIONS CONTAINING FLUORESCENT AGENTS

(76) Inventors: Thomas C. Simonton, Mount Wolf, PA (US); Kenneth S. Peterson, Lancaster, PA (US)

(*) Notice: Subject to any disclaimer, the term of this patent is extended or adjusted under 35 U.S.C. 154(b) by 0 days.

(21) Appl. No.: 12/939,342

(22) Filed: Nov. 4, 2010

(65) Prior Publication Data
US 2011/0045443 A1 Feb. 24, 2011

Related U.S. Application Data

(63) Continuation of application No. 11/541,065, filed on Sep. 29, 2006, now abandoned.

(60) Provisional application No. 60/721,706, filed on Sep. 29, 2005.

(51) Int. Cl.
*A61L 33/00* (2006.01)

(52) U.S. Cl. ...... 427/2.1; 427/2.24; 427/2.26; 427/2.27; 427/243; 427/256; 427/287; 427/429

(58) Field of Classification Search ............ 424/49; 523/116, 115, 212; 427/145, 2.1
See application file for complete search history.

(56) References Cited

U.S. PATENT DOCUMENTS

| | | | |
|---|---|---|---|
| 4,303,701 A * | 12/1981 | Torgersen et al. | ............ 427/145 |
| 4,600,389 A | 7/1986 | Schwartz | |
| 4,645,455 A | 2/1987 | Kosmos | |
| 4,748,198 A | 5/1988 | Takahashi et al. | |
| 4,957,441 A | 9/1990 | Bryan | |
| 5,102,461 A | 4/1992 | Rheinberger et al. | |
| 5,211,748 A | 5/1993 | Robinson et al. | |
| 5,269,682 A | 12/1993 | Kesling | |
| 5,596,025 A | 1/1997 | Oxman et al. | |
| 5,698,020 A | 12/1997 | Salz et al. | |
| 6,063,830 A * | 5/2000 | Deguchi et al. | ............... 523/115 |
| 6,262,142 B1 * | 7/2001 | Wang et al. | ................... 523/116 |
| 6,391,281 B1 | 5/2002 | Rueggeberg et al. | |
| 6,444,725 B1 | 9/2002 | Trom et al. | |
| 6,528,555 B1 | 3/2003 | Nikutowski et al. | |
| 6,670,436 B2 | 12/2003 | Burgath et al. | |
| 7,114,951 B2 | 10/2006 | Sun et al. | |
| 2004/0161389 A1 * | 8/2004 | Gallis et al. | ..................... 424/49 |
| 2007/0166450 A1 | 7/2007 | Simonton et al. | |

FOREIGN PATENT DOCUMENTS

| | | |
|---|---|---|
| DE | 29620554 U1 | 3/1997 |
| DE | 20012901 U1 | 1/2001 |
| GB | 1428672 A | 3/1976 |
| GB | 2190917 A | 5/1986 |
| GB | 2230271 A | 3/1989 |
| WO | 2007041477 A2 | 4/2007 |

\* cited by examiner

*Primary Examiner* — Dah-Wei Yuan
*Assistant Examiner* — Andrew Bowman
(74) *Attorney, Agent, or Firm* — Douglas Hura; Leana Levin; David Zdurne

(57) ABSTRACT

A method of applying a dental composition to tooth surfaces is provided. The dental composition, comprising polymerizable resin and fluorescing compound, is applied to a tooth surface and cured so that it hardens. The composition is preferably used as a dental sealant that provides a hard, glossy surface finish over a tooth. Upon irradiating the sealant with ultraviolet light, the sealant exhibits a bright fluorescent glow. The sealant reverts immediately to its natural color when it is no longer exposed to the ultraviolet light.

13 Claims, No Drawings

METHODS FOR USING DENTAL COMPOSITIONS CONTAINING FLUORESCENT AGENTS

CROSS-REFERENCE TO RELATED APPLICATIONS

This application is a continuation of U.S. Ser. No. 11/541,065 filed on Sep. 29, 2006, which claims the benefit of U.S. Provisional Application Ser. No. 60/721,706 having a filing date of Sep. 29, 2005, the entire contents of which are hereby incorporated by reference.

BACKGROUND OF THE INVENTION

1. Field of the Invention

The present invention relates generally to methods for using dental compositions containing polymerizable resins and fluorescent compounds. The dental compositions can be used as flowable composites (fillings), adhesives, sealants, and the like. The dental compositions are preferably used as dental sealants.

2. Brief Description of the Related Art

Dental professionals apply a sealant to the surface of a tooth in order to provide long-term protection against dental caries, which is caused by the accumulation of bacteria. The bacteria in plaque produce acids that eat into the tooth, eventually causing cavities to form therein. Pits and fissures may develop in the surface of a tooth, and bacteria tend to accumulate in these areas. Sealants are commonly used to fill the pits and fissures in the surface of a tooth, particularly the occlusal surfaces of posterior teeth. The sealants, once applied and cured, provide a smooth seal and prevent the ingress of fluids, food, and debris. The sealant can either have a clear composition or opaque composition to match the color of the tooth. Both types of sealant compositions tend to have a glossy surface finish and provide an aesthetically-pleasing appearance.

The dental professional must apply the sealant carefully so that it completely seals the pits and fissures in the surface of the tooth. Typically, the sealant is applied with a brush or other applicator. Then, the sealant is cured and hardened. The curing step normally involves irradiating the sealant with blue visible light having a wavelength generally in the range of about 400 to about 700 nm. The application and curing of the sealant can be difficult. When a clear sealant composition is used, the dentist may have trouble discerning between the pits and fissures, which need to be sealed, versus healthy dentition. It also can be difficult to apply an opaque sealant composition, because the color of the sealant composition and natural color of the tooth can be substantially the same. Another problem with some conventional sealants is that they tend to wear-away over time. When the dentist examines the patient in follow-up visits, he or she may not be able to easily detect if portions of the sealant have worn off. As part of an effort to address these problems, the dental industry has developed dental sealants containing fluorescing compounds. With these fluorescing sealants, the dental professional is better able to check margins and determine if the sealant has been placed accurately on the surface of the tooth during initial patient visits. In follow-up visits, the dentist can examine the patient's tooth, under fluorescing conditions, to determine if the sealant has worn off.

For example, Schwartz, U.S. Pat. No. 4,600,389 discloses dental compositions used for making restorations, inlays, onlays, crowns, sealants, glazes, and cements. The composition contains microbeads having a fluorescent rare earth chelated compound therein. The fluorescent rare earth compound is permanently isolated within the microbeads. The composition is colorless when viewed under ordinary daylight, sunlight, or disco light but is highly fluorescent when exposed to ultraviolet radiation having a wavelength of 300 to 400 nm according to the '389 patent.

Rheinberger et al., U.S. Pat. No. 5,102,461 relates to a colorless dental material that can be distinguished from natural teeth, false teeth, and other dental materials. The colorless dental material includes a fluorescent substance that emits fluorescent light as a result of being irradiated with radiation having a wavelength in the region of 360 to 480 nm. Suitable dental materials, which can be made in accordance with the '461 patent, include spacer varnishes, blocking materials, composite filling materials, cements, and sealants. The dental material is irradiated with light having a wavelength in the region of 360 to 480 nm, and the material is viewed through a light filter. The '461 patent teaches that the interfering effects caused by reflection of the irradiating light (360 to 480 nm) and the natural fluorescence of teeth are overcome by using the light filter.

Robinson et al., U.S. Pat. No. 5,211,748 discloses a dental restorative composition containing an additive that fluoresces under radiation having a wavelength in the visible light spectrum. The preferred additive is chromium-activated "crushed ruby." According to the '748 patent, a conventional light source, such as a blue light used for curing dental composites, can be used to irradiate the composition with the required visible light. The ruby additive fluoresces when irradiated by visible-wavelength light but does not fluoresce when irradiated by ultra-violet light.

Although some of the foregoing dental compositions can be used effectively as dental sealants, there is still a need for an improved composition. It would be particularly desirable to use a fluorescent compound, which does not impart any substantial color to the composition. The sealant, containing the fluorescent compound, would maintain its ordinary color after it had been applied to the surface of the tooth and while it was in an uncured condition. The sealant would maintain this same color after it had been cured. It also would be desirable to have a composition, which would fluoresce upon being irradiated with ultraviolet light, but would revert quickly to its ordinary color when it was no longer exposed to the ultraviolet light. The present invention provides a dental sealant having these desirable properties as well as other features and advantages.

SUMMARY OF THE INVENTION

The present invention provides a method of applying a dental composition to tooth surfaces. A dental composition comprising polymerizable resin and fluorescing compound is provided. The composition is applied to a tooth surface and cured so that it substantially hardens. Then, the composition is irradiated with a light source emitting light at a wavelength in the ultraviolet spectrum of about 200 to about 400 nm. The composition is visually identified by observing the composition emitting fluorescence having a wavelength in the visible spectrum of greater than about 400 nm. This allows the dental practitioner to distinguish the area of the tooth containing the composition from remaining natural areas of the tooth surface.

The fluorescent compound is preferably 7-diethylamino-4-methylcoumarin. The composition is preferably used as a dental sealant that provides a hard, glossy surface finish over a tooth. The sealant exhibits a bright fluorescent glow immediately upon being exposed to ultraviolet light. The sealant reverts immediately to its natural color when it is no longer exposed to the ultraviolet light. Only a low dosage of ultraviolet light is needed to excite the fluorescent compound in the composition.

DETAILED DESCRIPTION OF THE PREFERRED EMBODIMENTS

The present invention relates to methods of using a dental composition containing a polymerizable resin and fluorescent compound. Preferably, the dental composition is used as a sealant on tooth surfaces.

The dental composition of this invention contains a polymerizable resin such as, for example, acrylate resins, methacrylate resins, or mixtures thereof. Such acrylate and methacrylate resins are well known in the art and include, for example, polymerizable monomers and oligomers such as ethylene glycol di(meth)acrylate, diethylene glycol di(meth) acrylate, Methylene glycol di(meth)acrylate, tetraethylene glycol di(meth)acrylate, neopentyl glycol di(meth)acrylate, 1,3-butanediol di(meth)acrylate, 1,6-hexanediol di(meth) acrylate, trimethylolpropane tri(meth)acrylate, 2,2-bis[4-(2-hydroxy-3-acryloyloxypropoxy) phenyl]propane, 2,2-bis[4-(2-hydroxy-3-methacryloyloxypropoxy) phenyl]propane (Bis-GMA), 2,2-bis[4-(acryloyloxy-ethoxy)phenyl]propane, 2,2-bis[4-(methacryloyloxy-ethoxy)phenyl]propane, urethane di(meth)acrylate (UDMA), and the like.

In addition to the foregoing monomers and oligomers, the composition may contain diluent monomers such as hydroxy alkyl methacrylates; ethylene glycol methacrylates; and diol methacrylates such as tri(ethylene glycol) dimethacrylate (TEGDMA) to reduce viscosity and make the composition more suitable for application. The monomers and oligomers are typically present in the composition in an amount in the range of about 10% to about 99% based on the total weight of the composition and preferably in an amount in the range of about 20% to about 60%.

The composition can be self (chemically)-curable and/or light-curable. The composition may contain a photoactive agent such as, for example, benzophenone, benzoin and their derivatives or alpha-diketones and their derivatives in order to make the composition light-curable. A particularly preferred photoinitiator is camphorquinone (CQ). Preferably, photopolymerization is initiated by irradiating the composition with blue, visible light preferably having a wavelength in the range of about 400 to about 500 nm. A standard dental blue light-curing unit can be used to irradiate the composition.

The camphorquinone (CQ) compounds have a light absorbency maximum of between about 400 to about 500 nm and generate free radicals for polymerization when irradiated with light having a wavelength in this range. Alternatively, the photoinitiator can be selected from the class of acylphosphine oxides such as, for example, 2,4,6-trimethylbenzoyl-diphenyl-phosphine oxide. The photopolymerization initiators are typically present in the composition in the range of about 0.1 to about 10 wt. % and preferably in the range of about 0.1 to about 2 wt. %.

Furthermore, the composition may be self-curable and contain a polymerization initiator such as peroxide. For example, dibenzoyl peroxide, di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide, cumene hydroperoxide, and the like can be added to the composition. Polymerization accelerators, particularly tertiary amines also may be added to the composition to increase the rate of polymerization. In instances, where the composition will be cured by visible light, the tertiary amines are generally acrylate derivatives such as dimethylaminoethyl methacrylate, diethylaminoethyl methacrylate, and the like. In the self-curing compositions, the tertiary amines are generally aromatic tertiary amines such as, for example, N-methyl-diethanolamine, ethyl 4-(dimethylamino)benzoate (EDMAB), 2-[4-(dimethylamino)phenyl]ethanol, N, N-dimethyl-p-toluidine (DMPT), dihydroxyethyl-p-toluidine (DHEPT), bis(hydroxyethyl)-p-toluidine, triethanolamine, and the like.

In one form of the invention, the composition is provided as a paste-like material in a single package. In such instances, the composition typically is light-curable and contains a photoinitiator and polymerization accelerator as discussed above. Conventional dispensing syringes, applicators, brushes, and other delivery devices can be used to apply the composition to the desired area of the tooth or pre-existing dental restoration. In one embodiment, the composition is provided in a single cartridge, which is inserted into a barrel of a dispensing syringe. In practice, a dentist pushes on the plunger of the syringe to force the composition from the cartridge and through a dispensing tip. The composition is dispensed onto the targeted area of the tooth or dental restoration in this manner. Then, the composition can be cured or hardened by irradiating the composition with visible light radiation. A standard, visible blue light dental-curing unit can be used to cure the composition in this manner.

In another form of the invention, the composition is provided as a two-part, auto-curable system. A catalyst paste is provided in one package, and a base paste is provided in a second package. The catalyst paste may include a polymerizable monomer such as ethoxylated bisphenol-A-dimethacrylate and a catalyst such as dibenzoyl peroxide. The base paste may include a polymerizable monomer, which is different than the polymerizable monomer used in the catalyst paste, and a polymerization accelerator such as a tertiary amine. The fluorescent compound used in the composition of this invention, as discussed in further detail, below, can be added to either the catalyst or base pastes or both pastes. An auto-mix delivery system such as, for example, a double barrel syringe, can be used to mix the catalyst and base components and dispense the resulting composition. The catalyst and base pastes are stored in separate cartridges and dispensed from the cartridges in a pre-determined volume ratio and mixed together to form the composition. The resulting, mixed composition is delivered through the dispensing tip of the syringe and onto the targeted area. As the catalyst and base pastes are mixed together, the amine and peroxide react with each other and initiate polymerization and curing of the composition. Thus, the dentist has only a short working time when using this two-part system. The catalyst and base pastes are not mixed together until just before the dentist is ready to apply the composition.

In other instances, the catalyst and base pastes can be stored in separate applicator tubes. The catalyst and base pastes are dispensed from their respective applicator tubes and into a mixing dish. Then, the catalysts and base pastes can be mixed together by hand to form the final composition that will be applied to the tooth or dental restoration.

The dental composition may further contain conventional organic or inorganic fillers. Alternatively, the composition may be unfilled. Examples of conventional fillers include glass, quartz, barium borosilicate, strontium borosilicate, borosilicate, barium silicate, strontium silicate, lithium silicate, lithium alumina silicate, calcium phosphate, alumina, zirconia, tin oxide, titanium dioxide, and the like. Such fillers typically have a particle size in the range from about 0.1 to about 5.0 microns and are silane-treated in order to improve the bonding between the fillers and resin matrix. The composition is typically partially filled, and the amount of filler particles in the composition is typically in the range of about 10% to about 70% based on the total weight of the composition and preferably in the range of about 20% to about 60%. In other embodiments, the dental composition is unfilled, and there are no filler particles present in the composition.

The dental composition of this invention contains a fluorescent compound that is highly emissive and will impart a fluorescent glow to the composition when irradiated by an ultraviolet light source. The fluorescent compound is preferably 7-diethylamino-4-methylcoumarin. Several factors need to be considered when adding the fluorescent compound to the sealant composition. As in the case of many added components, the fluorescent compound can have both a positive and negative impact on the properties of the final composition. This potential trade-off in properties makes it difficult to add such components.

For example, adding a relatively low amount of fluorescent compound is economically advantageous, but it will not provide the sealant composition with sufficient fluorescence. On the other hand, adding a relatively high amount will impart a glowing fluorescence to the composition, but such high amounts also can cause deleterious changes to the physical properties of the composition. Particularly, the mechanical strength and wear-resistance can be reduced if a very high amount of fluorescent compound is added. Additionally, the fluorescent compound may impart some undesirable color to the composition.

Of the many possible fluorescent compounds that could be added to the composition, it was found that 7-diethylamino-4-methylcoumarin provides the most desirable properties. The 7-diethylamino-4-methylcoumarin is added in an amount effective to impart sufficient fluorescence to the composition. The amount of 7-diethylamino-4-methylcoumarin in the composition is not particularly restricted, and generally will be in the range of about 0.01 to about 15.00 weight percent (wt. %). But, it was found unexpectedly that only about 0.20 percent by weight (wt. %) of 7-diethylamino-4-methylcoumarin is needed to provide sufficient fluorescence. Moreover, it was found that adding 0.20 wt. % of 7-diethylamino-4-methylcoumarin does not negatively impact the physical properties or change the color of the composition.

Energy in the ultraviolet light spectrum is used to excite the fluorescent compound. Once excited, the fluorescent compound will emit energy in the visible light spectrum at a level sufficient to provide a bright, fluorescent glow. As a result, the dentist can easily identify the areas on the surface of the tooth, where the sealant composition has been applied. The dentist can make a visual distinction between pits and fissures, which have been filled with the fluorescent sealant, over natural areas of dentition. The fluorescent glow of the sealant allows the dentist to better check margins and accurately apply the sealant to only those areas of the tooth, where treatment is needed. During follow-up visits with the patient, the dentist can irradiate the tooth with ultraviolet radiation. Under these fluorescing conditions, the sealant, if present on the tooth, will exhibit a bright, fluorescent glow. This feature allows the dentist to determine if the sealant has worn away from any areas of the tooth.

As discussed above, the compositions of this invention are preferably used as dental sealants. It is contemplated that the above-described fluorescent compounds could be added to commercially-available dental sealant compositions such as, for example, DELTON; DELTON PLUS; and DYRACT (Dentsply International); BISCOVER (Bisco, Inc.); SEAL-N-SHINE (Pulpdent Corp.); and OPTIGARD (Kerr Manufacturing). Other commercial dental sealant compositions can be used in accordance with this invention.

In addition to the fluorescent compounds, the composition can contain additives such as flavoring agents, anti-microbial agents, plasticizers, anti-oxidants, viscosity modifiers, and the like. Preferably, a fluoride-releasing agent or filler is added to the composition. For example, a fluoride-releasing glass such as fluoro-alumino-silicate may be added to the composition. The fluoride-releasing glasses provide the benefit of long-term release of fluoride. Fluoride salts such as, for example, sodium fluoride also can be used in the composition. One benefit with adding a fluoride source to the composition is that the fluoride provides added protection against acid attack that causes tooth decay. The composition may contain a mixture of fluoride-releasing glasses and fluoride salts to provide a staged period of fluoride release. For example, the sodium fluoride or other fluoride salt can be added to provide a quick burst of fluoride. To complement the fluoride salt, a fluoridated glass, which provides a longer, slower rate of fluoride release, can be added.

The compositions of this invention can be used as various dental materials including, for example, as flowable composites (fillings), adhesives, sealants, and the like. Preferably, the composition is used as a dental sealant for sealing pits and fissures in the surface of a tooth. The sealant can have either a clear or opaque composition. The sealant is applied to the surface of the tooth so that it provides a smooth and glossy surface finish. The sealant coating is hard and non-tacky. In addition, the sealant coating has good mechanical strength, wear-resistance, and adhesion strength. The sealant may be applied to the surface of a tooth using methods well known in the art. First, the surface of the tooth is cleaned thoroughly. Prophylaxis pastes can be used to clean the surface of the tooth. Secondly, the surface of the tooth is dried with cotton rolls, an air syringe, or other appropriate materials. Thirdly, the surface of the tooth is acid-etched. Liquid etchant can be brushed onto the surface of the tooth to prepare an etched surface. Then, the surface of the tooth is dried again. Fourthly, the sealant is applied to the etched surface of the tooth with a brush or other suitable applicator. The uncured dental sealant has a syrup-like consistency. The dental sealant of this invention preferably has an off-white color. But, it should be recognized that the sealant might be formulated so that it has any suitable color. Colorants may be added to the sealant composition to modify the color as desired. The fluorescing compound imparts no substantial color to the sealant. Finally, the sealant is cured by irradiating it with visible blue light having a wavelength in the range of about 400 to about 800 nm. A standard blue light dental-curing lamp can be used to cure the sealant. The color of the sealant remains substantially the same even when the sealant has been cured with visible light. For example, if the sealant has a natural off-white color when it is in an uncured state, its color will remain off-white after the curing step has been completed.

When the dentist wishes to check the placement of the sealant, he or she irradiates the sealant with ultraviolet light having a wavelength in the range of about 200 nm to about 400 nm. Preferably, ultraviolet light having a wavelength in the range of about 365 nm to about 390 nm is used. As discussed above, energy in the ultraviolet light spectrum is used to excite the fluorescent compounds. In turn, the fluorescent compounds, will emit energy in the visible light spectrum at a level sufficient to provide a fluorescent glow, particularly a bluish-white fluorescent glow. The response to the ultraviolet light is immediate. An unaided human eye instantaneously sees the fluorescent glow of the sealant composition once the composition is exposed to ultraviolet light. The fluorescent glow of the composition is bright and clear, and a human observer can immediately discern materials that contain the composition over non-fluorescing materials. Moreover, the dentist can inspect a tooth and easily distinguish between the areas of the tooth, which have been treated with the sealant of this invention, versus those areas, which have not been treated with the sealant. The dentist removes the ultraviolet light source after completing his or her examination of the patient. Immediately at this point, when the tooth is no longer exposed to the ultraviolet light, the sealant reverts to its ordinary color (for example, off-white). The response to removing the ultraviolet light source is instantaneous. An unaided human eye will instantaneously observe the natural color of the sealant composition once the ultraviolet light source has been removed.

Any light source, which emits ultraviolet light, such as, for example, lamps, flashlights, lasers, light-emitting diodes, and the like can be used to illuminate the sealant composition of this invention. For example, a light-emitting, stylus-like device can be used as the ultraviolet light source. The stylus-like device is preferably lightweight and battery-operated. The stylus-like device contains light-emitting diodes that emit ultraviolet radiation. Generally, such stylus-like devices are easier to handle and operate than standard visible-light dental curing lamps. Furthermore, since the compositions of this invention respond immediately upon being exposed to the ultraviolet light, only a low dosage of ultraviolet radiation is needed. A dentist can grasp the stylus-like device and focus the ultraviolet light directly on the tooth or dental restoration. The dentist will immediately observe a fluorescent glow emanating from the tooth or restoration if the composition is present thereon.

The dental compositions of the present invention have many advantageous properties and benefits including the following. First, the composition exhibits a fluorescent glow immediately upon being exposed to the ultraviolet light. Conversely, when the composition is no longer exposed to the ultraviolet light, it reverts immediately to its natural color. In other words, the composition has an instantaneous on/off fluorescence mechanism. Secondly, the fluorescing compound imparts no substantial color to the sealant. Adding the fluorescent compound to the sealant composition does not change the natural color of the composition. Thirdly, a light-emitting, stylus-like device can be used as the ultraviolet light source. The device is preferably lightweight and battery-operated. Only a low dosage of ultraviolet energy is needed to excite the fluorescent compounds so that the composition gives off a fluorescent glow. Fourthly, the amount of fluorescent compound, which needs to be added to the composition to impart sufficient fluorescence, is relatively low. In general, only about 0.2 percent by weight (wt. %) of fluorescent compound is needed in accordance with this invention.

The invention is further illustrated by the following Examples, but these Examples should not be construed as limiting the scope of the invention.

EXAMPLES

Example 1

A dental sealant composition as described in below Table 1 was prepared.

TABLE 1

| Component | Weight Percentage (Wt. %) |
| --- | --- |
| Mixture of Bis-GMA, urethane modified Bis-GMA dimethacrylate, and dimethacrylate resin | 58.50% |
| Silanated barium-fluoro-alumino borosilicate glass | 38.00% |
| Titanium dioxide | 0.70% |
| Sodium fluoride | 2.00% |
| Silicon dioxide | 0.60% |
| 7-diethylamino-4-methylcoumarin | 0.20% |

The ingredients were introduced into a planetary mixer at ambient temperature and mixed together. After the ingredients were mixed for one hour, they were processed through a colloid mill to break-up any agglomerates. Lastly, the composition was mixed under vacuum to remove any entrained air.

The resulting sealant composition was applied as a sealant to a set of mounted, extracted teeth that were used as test specimens. The composition was tested for fluorescence in its uncured and cured states. An ultraviolet light source was used to illuminate the sealant-coated teeth. The composition immediately exhibited a fluorescence glow upon being exposed to the ultraviolet light. The fluorescent regions of the tooth, where the sealant composition had been applied, were easily identifiable and distinguishable over natural dentition of the tooth. Once the ultraviolet light source was removed and the tooth no longer illuminated, the sealant composition immediately reverted to its natural off-white color. In addition, the sealant composition was tested for various physical properties and the results are reported below in Table 3.

Comparative Example A

For comparison purposes, a sealant composition, which did not contain a fluorescent compound, was prepared and tested.

The formulation described in below Table 2 was used to prepare the comparative sealant composition. The comparative sealant composition was prepared in the same manner used to prepare the composition in Example 1.

TABLE 2

| Component | Weight Percentage (Wt. %) |
| --- | --- |
| Mixture of Bis-GMA, urethane modified Bis-GMA dimethacrylate, and dimethacrylate resin | 58.70% |
| Silanated barium-fluoro-alumino borosilicate glass | 38.00% |
| Titanium dioxide | 0.70% |
| Sodium fluoride | 2.00% |
| Silicon dioxide | 0.60% |

The above-comparative sealant composition was applied as a sealant to a set of mounted, extracted teeth that were used as test specimens. The composition was tested for fluorescence in its uncured and cured states. An ultraviolet light source was used to illuminate the sealant-coated teeth. The composition did not exhibit any fluorescence glow. In addition, the comparative sealant composition was tested for various physical properties and the results are reported below in Table 3.

TABLE 3

| Property | Example A (no dye) | Example 1 (dye added) |
|---|---|---|
| Diametral Tensile (PSI) | 7158 | 7100 |
| Water Sorption at 37° C. (mg/cm) | 0.9 | 0.7 |
| Uncured Film Thickness, % | 0.7 | 0.6 |
| Depth of Cure (mm) | 4 | 4 |
| Compressive Strength (PSI) | 44,570 +/− 3113 | 44,563 +/− 8734 |
| Abrasion (% Weight Loss) | 5.40 +/− 0.72 | 5.09 +/− 0.86 |
| Shear Bond Strength to Enamel (1800 Thermocycles, MPa) | 19.4 +/− 2.9 | 20.2 +/− 4.0 |

As shown in Table 3, there is no significant difference in the physical properties of the sealant composition of Example 1 that contains the fluorescent compound, 7-diethylamino-4-methylcoumarin; and the sealant composition of Comparative Example A that does not contain the fluorescent compound. Example 1 and Comparative Example A demonstrate that the fluorescent compound used in the sealant compositions of this invention does not interfere with the mechanical strength or other physical properties of the compositions.

Workers skilled in the art will appreciate that various modifications can be made to the illustrated embodiments and description herein without departing from the spirit and scope of the present invention. It is intended that all such modifications within the spirit and scope of the invention be covered by the appended claims.

What is claimed is:

1. A method of applying a dental composition to an area of a tooth surface, comprising the steps of:
   a) providing a dental composition comprising polymerizable resin and fluorescing compound, wherein the fluorescing compound includes 7-diethylamino-4-methylcoumarin;
   b) applying the composition to a tooth surface;
   c) curing the composition so that it hardens;
   d) irradiating the composition with a light source emitting light at a wavelength in the ultraviolet spectrum of about 200 to about 400 nm; and
   e) visually identifying the composition by observing emitted fluorescence having a wavelength in the visible spectrum of greater than about 400 nm so as to distinguish the area of the tooth surface containing the composition from remaining natural areas of the tooth surface.

2. The method of claim 1, wherein the polymerizable resin is selected from the group consisting of acrylate and methacrylate resins and mixtures thereof.

3. The method of claim 1, wherein the composition is light-curable and comprises a photoinitiator.

4. The method of claim 3, wherein the photoinitiator is camphorquinone.

5. The method of claim 1, wherein the composition is self-curable and comprises a polymerization initiator.

6. The method of claim 5, wherein the polymerization initiator is peroxide.

7. The method of claim 1, wherein the composition further comprises a filler material selected from the group consisting of organic and inorganic fillers.

8. The method of claim 7, wherein the filler material is fluoro-alumino borosilicate glass.

9. The method of claim 1, wherein the composition further comprises sodium fluoride.

10. The method of claim 1, wherein the 7-diethylamino-4-methylcoumarin is about 0.2 percent by weight of the dental composition.

11. The method of claim 1, wherein the fluorescing compound is in the range about 0.2 percent by weight to about 15 percent by weight of the dental composition.

12. The method of claim 1, wherein the fluorescing compound is present in an amount sufficient to provide fluorescence when exposed to the light source emitting light in the ultraviolet spectrum of about 200 to about 400 nm without changing the color of the dental composition when the light source is not emitting light in the ultraviolet spectrum of about 200 to about 400 nm.

13. A method of applying a dental composition to an area of a tooth surface, comprising the steps of:
   a) providing a dental composition comprising polymerizable resin and fluorescing compound, wherein the fluorescing compound does not impart color to the dental composition and wherein the fluorescing compound is 7-diethylamino-4-methylcoumarin and is present as about 0.2 percent by weight of the dental composition;
   b) applying the composition to a tooth surface;
   c) curing the composition so that it hardens; and
   d) irradiating the composition with a light source emitting light at a wavelength in the ultraviolet spectrum of about 200 to about 400 nm to cause emitted fluorescence having a wavelength in the visible spectrum of greater than about 400 nm.

* * * * *